(12) United States Patent
Bhakuni et al.

(10) Patent No.: US 6,683,193 B2
(45) Date of Patent: Jan. 27, 2004

(54) SINGLE POT CONVERSION OF ARTEMISININ INTO ARTEMETHER

(75) Inventors: Rajendra Singh Bhakuni, Lucknow (IN); Tarun Singh, Lucknow (IN); Atul Prakash Kahol, Lucknow (IN); Amit Tewari, Lucknow (IN); Sundeep Tandon, Lucknow (IN); Suman Preet Singh Khanuja, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/105,964

(22) Filed: Mar. 25, 2002

(65) Prior Publication Data

US 2003/0181513 A1 Sep. 25, 2003

(51) Int. Cl.$^7$ ............................................. C07D 323/00
(52) U.S. Cl. ...................................................... 549/348
(58) Field of Search ........................... 549/348; 514/450

(56) References Cited

PUBLICATIONS

Haynes et al, Chem. Absract vol. 121 No. 238135, "Extrsaction of artemisinin and artemisnic acid", 1994.*

* cited by examiner

Primary Examiner—Alan L. Rotman
Assistant Examiner—Raymond Covington
(74) Attorney, Agent, or Firm—Ladas & Parry

(57) ABSTRACT

The present invention relates to an improved method for the preparation of Artemether. Artemether prepared from the process is useful for the treatment of uncomplicated, severe complicated and multi drug resistant malaria.

16 Claims, 1 Drawing Sheet

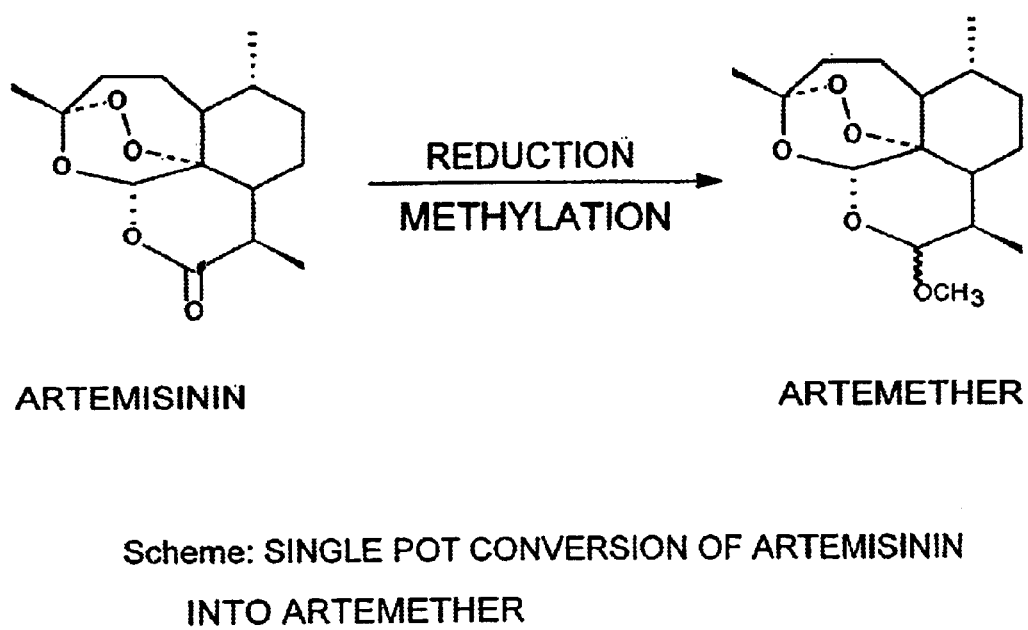
Scheme: SINGLE POT CONVERSION OF ARTEMISININ INTO ARTEMETHER

SINGLE POT CONVERSION OF ARTEMISININ INTO ARTEMETHER

FIELD OF INVENTION

The present invention relates to an improved method for the preparation of Artemether. Artemether prepared from the process is useful for the treatment of uncomplicated, severe complicated and multi drug resistant malaria.

BACKGROUND OF THE INVENTION

Approximately, out of the 4 billion people suffering from malaria, 1–3 million, mostly children die every year worldwide. The rapidly spreading multidrug resistant parasite to standard quinoline based antimalarial drugs such as chloroquine and mefloquine based antimalarial complicate chemotherapy treatment of malaria patients.

Artemether is a methyl ether derivative of dihydroartemisinin. Dihydroartemisinin is derived from arternisinin, a novel sesquiterpene endoperoxide isolated from the plant *Artemisia annua*. Artemisinin and its derivative artemether, arteether, artelinate and artesunate a novel class of antimalarials derived from *Artemisia annua* are now proving their promising activity and being used for the treatment; of uncomplicated severe complicated/cerebral and multi drug resistant malaria.

Artemether, developed in France and China has undergone extensive preclinical, animal, toxicological studies as well as clinical studies. Artemether is more potential as compared to artemisinin and an antimalarial drug especially for treating multi drug resistant and complicated strains of *Plasmodium falciparum*.

Artemether shows rapid shizonticidal action with quicker parasite clearance rate, short half life less side effect and low recrudence rate. Brossi, et al (Brossi, A; Venugopalan, B, Domingueg, G L; Yeh, H. J. C; Flippend-Anderson, J. L.; Buchs, P; Luo, X. D.; Milhous,W and peters, W; J. Med. Chem. 31, 646–649, 1988) reported the preparation of arteether, the ethyl ether derivative of dihydroartemisinin in two steps: First artemisinin was reduced with an excess of sodium borohydride in methanol at 0 to −5 degree C. in 3 hours to dihydroartemisinin in 79% yield. In the second step arteether is prepared by dissolving the dihydroartemisinin in the solvent mixture of benzene and ethanol at 45 degree C. followed by addition of $BF_3$ etherate and refluxing the reaction mixture at 70 degree C. for one hour. After completion of the reaction it was worked up, dried over anhydrous sodium sulphate with removal of the solvent dichloromethane. The reaction yielded arteether along with some impurities. Column chromatography of the reaction mixture over silica gel, 1:20 ratio yielded pure alpha and beta arteether in nearly qualitative yield.

EL-Feraly etal. (E L Feraly, F. S; Al-Yahya M A; Orabi, K. Y; Mc-Phail D R and Me Phail A. T. J.Nat.Prod. 55, 878–883 1992) reported the preparation of arteether by a process in which anhydrodihydroartemisinin, prepared from artemisinin was dissolved in absolute alcohol. The reaction mixture was stirred in the presence of p-toluene sulphonic acid used as a catalyst. On workup it yielded a mixture of beta arteether and C-11 epimer in the ratio of 3:1. In this process only beta arteether, is obtained and separation of C-11 epimer is difficult and preparation of anhydrodihydroartemisinin is a tedious process. The reaction took 22 hours to complete. The lewis acid catalyst used in this reaction is required in large amount (60 mg. acid catalyst by 100 mg. anhydrodihydroartemisinin).

In another method Bhakuni etal (Bhakuni, R. S.; Jain D. C and Sharma R. P. Indian. J. Chemistry, 34B, 529–30, 1995) arteether, artemether and other ether derivatives were prepared from dihydroartemisinin in different alcohol and benzene in the presence of chlorotrimethylsilane catalyst in 2–4 hours at room temperature. After workup of the reaction mixture and removal of the solvent, the impure reaction products were purified over silica gel column to obtained the pure mixture of alpha, beta ethers.

Another method is reported by Lin et al. (Lin, A. J. and Miller, R. E, J.Med Chero. 38,764–770, 1995) In this method the new ether derivatives were prepared by dissolving dihydroarternisinin in anhydrous ether and appropriate alcohol followed by $BF_3$-etherate. The reaction mixture was stirred at room temperature for 24 hours. The yield of the purified products ranged from 40–90%. Purification was achieved by the use of silica gel chromatography.

Another method described by Jain et al (Jain D. C, Bhakuni R. S, Saxena S, kumar, S and Vishwakarma, R. A.) the preparation of arteether from artemisinin comprises: Reduction of artemisinin into dihydroartemisinin. Isolation of dihydroartemisinin. Acylation of dihydroartemisinin by dissolving it in alcohol and adding trialkylorthoformate in the reaction mixture, which produce ethers in quantitative yield in 10 hours at 40 degree C.

The above mentioned methods carry some disadvantages being less cost effective and more time consuming as compared to the present invention. Moreover, benzene, a carcinogenic solvent, used in the previous methods is not acceptable according to the health standard. Further, all the above methods require at least two separate steps to convert artemisinin into ethers i.e. reduction of the artemisinin into dihydroartemisinin in the first pot followed by isolation of dihydroartemisinin and then comes the second step of conversion of dihydroartemisinin into different ethers in the second pot. However, the present invention provide an efficient method for conversion of artemisinin into artemether.

OBJECTS OF INVENTION

The object of the present invention is the development of cost effective and improved single step method for the preparation of artemether which possesses reduction of artemisinin into dihydroartemisinin followed by methylation of dihydroartemisinin into artemether in a single pot.

SUMMARY OF THE INVENTION

The present invention provide a method for the preparation of artemether from artemisinin in one pot in just about 4 hours. It comprises: Reduction of artemisinin with less quantity of sodium borohydride in methanol at 0 to −5 degree C. into dihydroartemisinin which occurs without isolation of the methylated (metherified) product in the presence of solid/liquid acid catalyst in the same pot at room temperature. After usual workup, the impure artemether purified by silica gel column chromatography in 1:5 ratio, yielded 80–82% (w/w) pure alpha, beta artemether.

BRIEF DESCRIPTION OF THE DRAWING

The drawing is a schematic representation of the single pot conversion of artemisinin into artemether.

DETAILED DESCRIPTION OF THE INVENTION

An improved single step process for the preparation of artemether from artemisinin in one pot comprising the steps of:

a. dissolving artemisinin in dry methanol at room temperature,
b. adding sodium borohydride and stirring of the reaction mixture at 0 to −5 degree C. for about 2 hours,
c. adding an acid catalyst (solid/liquid) at cooling temperature,
d. stirring of the reaction mixture further for about 2 hours at room temperature,
e. adding cooled water to the reaction mixture,
f. filtering the solid catalyst and neutralizing the filtrate or reaction mixture with 5% sodium bicarbonate solution,
g. extracting the reaction product with a solvent such as dichloromethane,
h. drying the extract over anhydrous sodium sulphate and evaporating the solvent, and
i. purifying the artemether over silica gel column in hexane-ethyl acetate to obtain pure alpha and beta artemether.

In an embodiment, the two reactions, reduction of artemisinin into dihydroartemisinin and methylation of dihydroartemesinin into artemether are carried out in a single pot thereby avoiding the unwanted process of isolation of dihydroartemisinin.

In another embodiment, the conversion of artemisinin into artemether is completed in about 4 hours in one pot and is cost effective.

In still another embodiment, the dihydroartemisinin is not required to be isolated The dihydroartemisinin is produced in situ In another embodiment, methanol is used as solvent for both reduction and methylation reaction as well as reactant in methylation reaction.

In yet another embodiment, the artemisinin and sodium borohydride are used in 4–5:1 ratio w/w.

In an embodiment, the liquid acid catalyst is selected from trifluroacetic acid and chlorotrimethylsilane.

In another embodiment, the artemisinin and liquid acid catalysts are used in 1:8 w/v.

In still another embodiment, the solid acid catalyst is selected from cation exchange resin.

In an embodiment, the ratio of artemisinin and solid cation exchange resin is 1:3 w/w.

In another embodiment, the reduction reaction is stirred at 0 to −5 degree C. and methylation reaction at room temperature (23 degree C.).

In yet another embodiment, elution of the column is carried out with hexane-ethyl acetate in (96:4) to yield alpha and beta artemether is 80–82% w/w.

In still another embodiment, the resin used is regenerated and can be reused in the further reaction.

To describe in detail, in the process of invention, artemisinin is dissolved in dry methanol and the solution was cooled to −5 degree C. Now sodium borohydride is added slowly and the reaction mixture is stirred for about 2 hours.

After completion of the reduction of artemisinin, without workup or the isolation of the dihydroartemisinin, a solid acid catalyst, resin or liquid acid catalyst, chlorotrimethylsilane or trifluroacetic acid is added at cooling temperature and the reaction mixture is further stirred for about 2 hours at room temperature.

After completion of the methylation reaction, cooled water is added in the reaction. The solid catalyst is filtered and the filtrate or the reaction mixture is neutralized with 5% sodium bicarbonate solution followed by extraction of the reaction mixture with dichloromethane.

The extract is dried over anhydrous sodium sulphate and removal of the solvent furnishes impure artemether. Silica gel column chromatography (1:5 ratio) with 4% ethyl acetate in n-hexane furnishes pure alpha, beta artemether in 80–82% w/w yield.

The following examples are given by way of illustration of the present invention and should not be construed to limit the scope of the present invention.

EXAMPLE 1

Artemisinin (3 g.) was dissolved in dry methanol (40 ml) at room temperature. It was cooled to −5 degree C. Now sodium borohydride (700 mg) was added slowly for 30 minutes and the reaction mixture was stirred for about 1.5 hours. The reaction was monitored by TLC to check completion of the reduction step. Now cation exchange resin (8 g) was added slowly at cooling temperature and the reaction mixture was further stirred at room temperature for about 2 hours. Cooled water was added to the reaction mixture and the resin was filtered.

The filtrate was neutralized with 5% sodium bicarbonate solution followed by extracting with dichloromethane (3×50 ml). The dichloromethane extract was dried over anhydrous sodium sulphate and evaporation of the solvent yielded 3.21 g, of artemether along with some impurities. The impure artemether was purified over silica gel column (1:5 ratio) in hexane:ethyl acetate (96:4) furnished pure alpha and beta artemether 2.43 g (81% w/w). Small portion of artemether was separated by prep TLC into alpha and beta isomers and characterized by the analysis of their IR, Mass and $^1$H NMR data.

EXAMPLE 2

The experiment was carried out following example 1 except in place of solid acid catalyst in the second reaction. Liquid acid catalyst chlorotrimethylsilane was added at cooling temperature for methylation reaction. The overall yield of pure alpha, beta artemether after column chromatography was 2.46 gm (82% w/w).

EXAMPLE 3

Artemisinin (100 g.) was dissolved in dry methanol (3 ml). Added sodium borohydride (30 mg.) at −5° C. The reaction mixture was stirred for 2 hours. After completion of the reaction, trifluroacetic acid (0.5 ml) was added and the reaction mixture was stirred for 5 hours. The methylation was incompleted and after workup the artemether was purified by prep TLC to yield 46 mg (46%) pure alpha, beta artemether.

EXAMPLE 4

The experiment was carried following example 1 except before column chromatography, the beta isomer (40%) was recrystallized in hexane from impure artemether and remaining mother liquor was purified over silica gel column in 1:5 ratio to yield alpha and beta artemether in 80% w/w.

What is claimed is:
1. A process for the preparation of artemether from artemisinin comprising the steps of (a) dissolving the artemisinin in methanol, (b) reducing the artemisinin dissolved in methanol with sodium borohydride in a reaction vessel to produce a reaction mixture comprising dihydroartemisinin, (c) without isolating the dihydroartemisinin from the reaction mixture, adding an acid catalyst to the reaction mixture to cause conversion of the dihydroartemisinin to artemether, said steps (b) and (c) being conducted in a solvent consisting essentially of the methanol, and (d) recovering and purifying the artemether.

2. The process as claimed in claim 1, wherein the artemether comprises alpha and beta artemether, and the steps (a), (b), (c) and (d) are conducted so as to result in a yield of alpha and beta artemether of at least 80% w/w.

3. The process as claimed in claim 1, wherein a ratio of artemisinin to sodium borohydride in step (b) is between 4:1 and 5:1.

4. The process as claimed in claim 3, wherein steps (a) and (b) are completed in about 4 hours.

5. The process as claimed in claim 2, wherein step (a) is carried out at room temperature and step (b) is carried out at a temperature of 0 to −5 degrees C., with stirring, until completion of the reducing step.

6. The process as claimed in claim 5, wherein the acid catalyst is a solid acid catalyst.

7. The process as claimed in claim 6, wherein the recovering in step (d) comprises adding cool water to the reaction mixture and filtering the solid catalyst to form a filtrate, neutralizing the filtrate or the reaction mixture, extracting the reaction product with a solvent to form an extract and drying the extract over anhydrous sodium sulfate and evaporating the solvent.

8. The process as claimed in claim 7, wherein the purifying in step (d) is performed with a silica gel column in hexane-ethyl acetate.

9. The process as claimed in claim 5, wherein the acid catalyst is a liquid acid catalyst.

10. The process as claimed in claim 9, wherein the liquid acid catalyst is selected from the group consisting of trifluoroacetic acid and chorotrimethylsilane.

11. The process as claimed in claim 10, wherein the artemisinin and the liquid acid catalyst are present in step (c) in a ratio of 1:8 w/v.

12. The process as claimed in claim 6, wherein the acid catalyst is a solid cation exchange resin.

13. The process as claimed in claim 12, wherein the artemisinin and the solid cation exchange resin are present in step (c) in a ratio of 1:3 w/w.

14. The process as claimed in claim 13, wherein step (b) is carried out at 0 to −5 degrees C. with stirring and step (c) is carried out at room temperature.

15. The process as claimed in claim 14, further comprising regenerating the cationic exchange resin.

16. The process as claimed in claim 2, wherein the yield of alpha and beta artemether is between 80–82% w/w.

* * * * *